United States Patent [19]
Danylewych-May et al.

[11] Patent Number: 5,988,002
[45] Date of Patent: Nov. 23, 1999

[54] METHOD OF COLLECTING TRACE SAMPLES FOR ANALYSIS

[75] Inventors: Ludmila Danylewych-May, North York; John Henry Davies, Port Credit, both of Canada

[73] Assignee: Barringer Research Limited, Mississauga, Canada

[21] Appl. No.: 09/138,391

[22] Filed: Aug. 24, 1998

Related U.S. Application Data

[62] Division of application No. 08/627,196, Apr. 3, 1996, Pat. No. 5,859,375.

[51] Int. Cl.⁶ ........................................ G01N 1/14
[52] U.S. Cl. ........................................... 73/864.71
[58] Field of Search ............................ 73/863.21, 863.23, 73/863.25, 864.34, 864.71, 864.72

[56] References Cited

U.S. PATENT DOCUMENTS

| | | | |
|---|---|---|---|
| 3,066,342 | 12/1962 | Jackson et al. | 73/864.71 |
| 3,074,276 | 1/1963 | Moos | 73/864.71 |
| 3,091,967 | 6/1963 | Hurdlow et al. | 73/864.71 |
| 3,684,660 | 8/1972 | Kereluk et al. | 73/864.71 X |
| 3,748,905 | 7/1973 | Fletcher et al. | 73/863.25 |
| 3,897,688 | 8/1975 | Meserol et al. | 73/864.71 X |
| 3,970,428 | 7/1976 | Barringer . | |
| 4,192,176 | 3/1980 | Barringer . | |
| 4,220,414 | 9/1980 | Barringer | 356/318 |
| 4,426,214 | 1/1984 | Vandrish | 73/863.25 X |
| 4,909,090 | 3/1990 | McGown et al. | 73/864.33 |
| 5,071,771 | 12/1991 | Barbour et al. | 436/153 |
| 5,243,865 | 9/1993 | Hsu et al. | 73/864.72 |
| 5,333,511 | 8/1994 | Boyum et al. | 73/863.25 X |
| 5,425,263 | 6/1995 | Davies et al. | 73/28.05 |
| 5,476,794 | 12/1995 | O'Brien et al. | 436/92 |
| 5,517,866 | 5/1996 | Manning et al. | 73/863.21 |
| 5,571,976 | 11/1996 | Drolet | 73/864.71 |
| 5,741,984 | 4/1998 | Danylewycl-May et al. | 73/864.71 |
| 5,823,592 | 10/1998 | Kaliddindi | 73/864.71 X |

FOREIGN PATENT DOCUMENTS

| | | |
|---|---|---|
| 2 634 018 A1 | 1/1990 | France . |
| 2 660 873 | 10/1991 | France . |
| 2 708 740 A1 | 2/1995 | France . |
| 2 185 571 | 7/1987 | United Kingdom . |

Primary Examiner—Thomas P. Noland
Attorney, Agent, or Firm—Bereskin & Parr

[57] ABSTRACT

A hand held sampling method is carried out using apparatus have a handle, a head connected to the handle and a mechanism for retaining a substrate on the head. The substrate is preferably a sheet-form flexible substrate which is mounted so as to present a collection portion thereof for collection of a sample. The substrate is preferably of a dimension so as to be readily fitted into the inlet portion of an analyzer. The apparatus is manipulated so that the collection portion of the substrate traverses surfaces of interest. The substrate is then removed and placed at the inlet of an analyzer for desorption of a sample. The apparatus enables an area to be sampled quickly and efficiently, while keeping a user's hands away from the surface, and this enables otherwise inaccessible areas to be sampled. It does not require any intermediate transfer steps, transferring a sample from a collection media to another substrate for subsequent analysis.

13 Claims, 4 Drawing Sheets

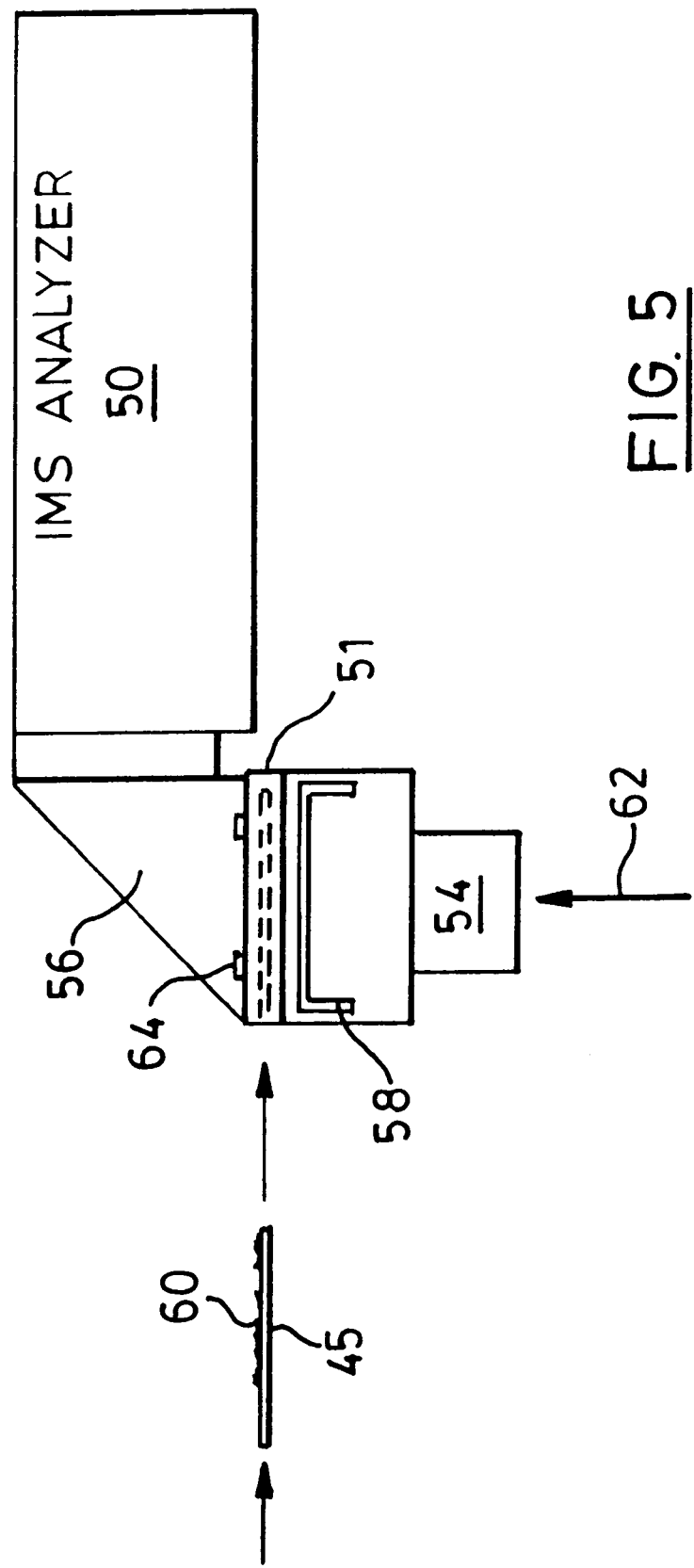

METHOD OF COLLECTING TRACE SAMPLES FOR ANALYSIS

This application is a Divisional application of application Ser. No. 08/627,196 filed Apr. 3, 1996 and now U.S. Pat. No. 5,859,375.

FIELD OF THE INVENTION

This invention relates to the collection from surfaces of samples of trace particles or liquids, or other compounds for chemical detection by various analytical means, such as an ion mobility spectrometer (IMS), gas chromatography (GC), liquid chromatography (LC), mass spectrometry (MS) and other methods, the compounds being present either as traces within particles or as discrete particles or aerosols, droplets or the like. The invention more particularly relates to the detection of explosives, narcotics, and other contraband concealed by individuals in their belongings or in transported goods and cargo, or in vehicles and aircraft. However, the invention also encompasses environmental sampling such as chemical warfare agent liquid droplets and aerosols which are extremely toxic and for which no hand contact can be tolerated.

BACKGROUND OF THE INVENTION

The removal of dust as a simple household task from domestic dwellings has been and is still carried out with dust cloths. In more sophisticated situations, chatelaines and housekeepers have employed maids, butlers and valets equipped with white gloves or mittens to remove dust, polish silverware and furniture. Previously, there has been no necessity or interest in analyzing the collected dust particles. Rather, the sole intent was to collect and throw out dust and dirt particles.

The necessity to collect dust and particles for analysis is a more recent requirement. With the advent of terrorism where explosives can be concealed to create undetectable bombs and also with drug smugglers concealing their drug shipments, the need for trace/forensic detection has become necessary. While early explosives detectors relied on the collection of atmospheric explosives vapours, modern high power explosives are plastic with extremely low vapour pressures thereby presenting vapour detection instruments with extremely difficult detection situations to the point of impossibility. Modern plastic explosives can have vapour pressures 5 or 6 orders of magnitude lower than the traditional volatile explosives such as nitroglycerine (NG), trinitrotoluene (TNT) and ethylene glycol denitrate (EGDN). For example, U.S. Pat. No. 4,909,090 teaches the use of hand operated vapour samplers which heats the surface to assist in dislodging vapours which are trapped on collector surfaces in the probe. However, with the very low vapour pressure of plastic explosives and drugs this method is extremely limited in its usefulness. Drugs like cocaine, heroine and others also have very low vapour pressures and thus are undetectable by existing vapour detection instruments.

Modern detection equipment can detect extremely low levels of explosives, narcotics and the like, in the range of nanograms or picograms. However, this simply raises the problem of obtaining a suitable sample. Accordingly, rather than attempt to collect a vapour sample, an alternative approach of particle collection and analysis was proposed, notably by Barringer, et al, and followed by others, both for forensics purposes as well as for surface geochemical exploration where trace metals and organometals can be useful as pathfinder indicators in mineral exploration activities. Earlier patents have covered these applications, such as Barringer U.S. Pat. Nos. 3,970,428; 4,220,414; 4,192,176; and 5,425,263.

Particle collection techniques include: surface inspection by means of physical particle collection in minute amounts; the use of dust pan-brush arrangements; vacuum suction onto porous or semi-porous substrates, filters, membranes and the like; the use of swabs, swipes, gloves, etc. One such method is described in U.S. Pat. No. 5,476,794 which describes the removal of particles with a glove and the use of an intermediate step, that of vacuum suction off the glove. These techniques have been the subject of earlier patents, which have developed into more sophisticated techniques incorporated into various instrumental devices for direct analysis, including plasma optical emission spectrometers, optical analyzers and mass spectrometers among others.

Gloves, mitts and swipes have been used in various forms for particle collection. Disadvantages exist with these earlier systems of collection. The major disadvantage of most of these earlier techniques is that an intermediate step is required to transfer from such a glove or the like any particles/trace chemicals so collected for presentation to the analytical device. One method is to use a suction device to vacuum the glove or mitt, as in U.S. Pat. Nos. 5,476,794. Not only does this present a loss of time and cause nuisance to the operator, but the secondary stage is inefficient, causing a loss of sample due to incomplete transfer from the glove. Additionally, vacuum suction devices are noisy, cumbersome, and require power to energize the suction motors. Even small vacuum hand samplers have relatively limited battery life. If a positive hit is obtained, then usually the suction device is contaminated and has to be cleaned thoroughly before being used again. Finally, often an even greater problem is created by the suction causing glove/cloth fibers and lint to be released which can either obstruct the collecting substrate, present interfering chemicals or fluff/ lint which might compete in the analytical process, as for example, if IMS is used where matrix effects from the hand covering material may well compete too aggressively in the ionization process.

Sampling materials or cloth which cover the fingers are also known for collecting particles from surfaces. These have the advantage of avoiding the intermediate step and use of a suction device. Such sampling cloths or finger covers unfortunately leave the fingers vulnerable to damage from sharp objects or exposed corners, hot objects or surfaces contaminated with toxic chemicals. Finger swabs/hand mitts can also become dislodged during search operations when pressed into tight areas.

Finally the problem of cross-contamination remains, in that if a hand/finger is in direct contact with the swab, or glove/mitt, there is always the possibility that the hand/ fingers will become contaminated with the analyte sought and pass this over as false positive alarms or hits onto subsequent samples. Also in some sampling situations, such as Chemical Warfare (CW) agents/liquid droplets, the chemical toxicity of the sample is too dangerous to allow close contact with hands.

As described in U.S. Pat. No. 5,476,794, particles are transferred from the glove to a collection probe, and the complete probe is inserted into the analyzer to vaporize the samples. The major disadvantage with this technique is the complexity of the sampling probe, the ease with which it can be clogged by debris and lint off gloves, and its complexity and hence cost.

An alternative means to collect trace particles is to use small filter discs which are inserted into the suction line of a vacuum cleaner unit to efficiently remove by suction the particles required for analysis. The substrate discs are positioned immediately at the sampling head to prevent particles lodging in the suction line and becoming dislodged at a later time thereby giving false anomalies. The collection substrate must be porous enough to allow air suction while at the same time be sufficiently dense to entrap the particles in the size range of interest. After a collection time adequate to collect a sufficient quantity of dust/material for analysis, the filter disc or substrate is removed and presented for analysis, as for example to an ion mobility spectrometer (IMS). The filter disc is inserted into a thermal desorption device which is rapidly heated to volatilize the collected material. The heating process converts the trace particles to vapours for conventional chemical vapour analysis, such as might be made by an IMS, mass spectrometer or gas chromatography or such other instrument.

The disadvantage of this technique is that it is still possible that the vacuum cleaner can become contaminated. More importantly, it requires manipulating a cumbersome vacuum cleaner to obtain a sample. Bearing in mind that only trace samples may be available, it is highly desirable to be able to quickly and efficiently gather particles from the surfaces of luggage, vehicles etc.

SUMMARY OF THE INVENTION

In accordance with earlier application Ser. No. 08/627,196, there is provided a hand held sampling apparatus for collecting a sample of at least one of solid particles, aerosols, droplets and trace chemicals on a substrate which is in sheet form and comprises a central working portion and an edge portion substantially extending around the central working portion, for analysis in an analyzer, the apparatus comprising: a handle; a head connected to and extending from the handle and including a bore and a retaining means for retaining the substrate within the bore, for presenting the working portion for collection of the sample and for enabling mounting and removal of the substrate from the apparatus, the head also including a projection means movable, relative to the retaining means, between an open configuration, spaced from the retaining means to permit insertion and removal of the substrate, and a closed configuration, in which the retaining means simultaneously traps the edge portion of the substrate between the retaining means and the projection means, with the projection means projecting through the bore whereby the working portion projects outwardly.

Advantageously, the head is connected to the handle by a shaft, which shaft spaces the head from the handle. Preferably, the projection means comprises a boss adapted to project through and beyond the bore.

To facilitate mounting and removal of the substrate, the boss is advantageously mounted on an arm or plate, which is pivotally mounted with respect to the handle.

The apparatus can include a light means within the projecting body for illuminating an area being sampled and/or a suction means connected to the holes for drawing air through the projecting body, to enhance collection of particles on a substrate.

The invention of that earlier application can be provided in combination with a substrate for collection of particles. The substrate is sheet form and comprises a central collection or working portion and an edge portion. More preferably, the substrate is chemically inert, is devoid of any dyes and colouring materials, and is such as to be capable of a mechanical wiping action, without removing from the substrate appreciable amounts of lint and fibers, and the substrate is capable of elevated temperatures for thermal desorption and pyrolysis processes. The substrate can be woven and can comprise one of cotton, Teflon, and fibreglass. The substrate can be chemically treated to enhance its ability to collect and entrap at least one of desired particles, droplets and chemical agents, and the substrate material can be chemically treated to modify the chemistry thereof during desorption, and pyrolysis cycles.

The invention provides a method of collecting a sample of at least one of particles, aerosols, droplets and trace chemicals, the method comprising the steps of:

(1) providing a substrate having a central working portion and an edge portion substantially extending around the working portion and mounting the substrate in a hand held sampling apparatus comprising a handle, a head connected to the handle and means retaining the substrate, by the edge portion of the substrate, on the head, so that the working portion of the substrate is presented for use;

(2) manipulating the apparatus so that the collection portion of the substrate traverses surfaces of interest;

(3) removing the substrate from the apparatus and inserting the substrate into the inlet port of an analyzer;

(4) operating analyzer to desorb any sample collected and analyzing the sample.

In step (3) the substrate is removed by grasping an edge portion thereof, without contacting the working portion.

It is expected that the present invention will provide a consistent degree of performance and reliability in the collection of dust/particles, aerosols or droplets required for analysis. While the invention is expected to have particular applicability to collection of particles of explosives and drugs, it is not restricted to this and may be of use on other compounds which may be aerosol or liquid, as for example, which can be experienced CW agent detection, the verification of decontamination, etc.

Since the substrate does not continuously contact the hands/fingers and need not contact them at all, possible allergies effects are prevented. It is known that latex gloves and fibreglass can cause allergies to the hands of the searchers.

Finally, the use of the substrate holder allows several such samples to be in use in conjunction with one analyzer. If hand swabs/gloves/mitts are used, general operational practice is that one should await the result of the swab analysis before proceeding to the next sample to avoid the possibility of contamination, a situation which does not occur with the present apparatus since each sample is unique and presented as such for analysis. It is known that if multiple objects are being sampled any trace particles picked up on one object/surface can be transferred off the glove/mitt to the second or subsequent object/surfaces, which can cause considerable difficulties in the searching procedures.

BRIEF DESCRIPTION OF THE DRAWINGS

For a better understanding of the present invention and to show more clearly how it may be carried into effect, reference can now be made, by way of example, to the accompanying drawings, in which:

FIG. 5 is a schematic view showing an inlet of an IMS analyzer and insertion of a substrate for analysis.

DESCRIPTION OF THE PREFERRED EMBODIMENTS

Figure 1A:
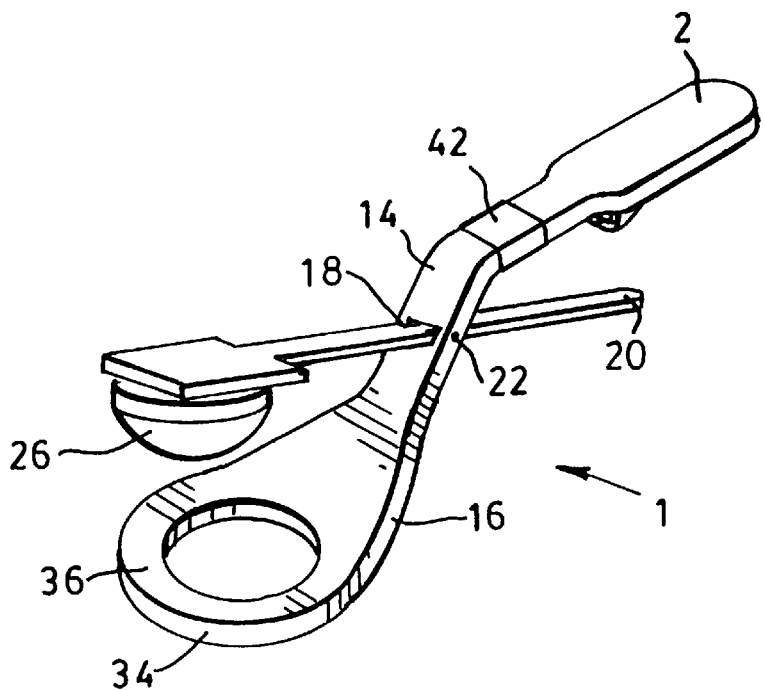
FIG. 1a is a perspective view of a first embodiment of a collection device in accordance with the present invention.
Figure 1B:
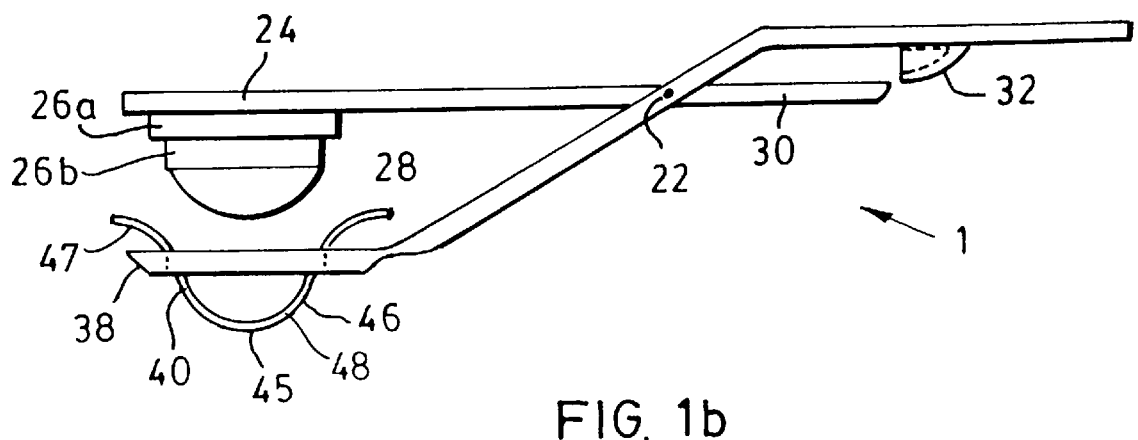
FIG. 1b is a side view of the first embodiment.

Referring first to FIG. 1, a first embodiment of the apparatus for carrying out the present invention is generally denoted by the reference 10. The apparatus 10 has a handle 12. Extending from the handle 12 is a shaft 14, and at the end of the shaft 14, a head 16. The handle is shaped to provide easy and comfortable operation, while spacing the user's hand from the operating head 16, as detailed below, so as to protect the hand from injury and contamination.

The shaft 14 includes a slot 18 through which extends a substrate retaining arm 20. A pin 22 connects the retaining arm 20 to the shaft 14 and provides a pivotal connection.

A first, outer end 24 of the arm 20 includes a resilient protrusion or boss 26, which comprises a base portion 26a and a resilient, sponge layer 26b. A disposable pad 28 is mounted on the sponge layer 26b, by any suitable means. The pad 28 and layer 26b together are resilient enough to enable a substrate to closely follow a surface under inspection.

A second end 30 of the arm 20 is adapted to engage a retaining clip 32. The clip 32 can comprise any suitable clip arrangement, including a simple spring clip or some hinged catch or lever. The arm 20 is shown in an open configuration, with the protrusion 26 raised to permit insertion and removal of a substrate. In the closed configuration (not shown), the second end 30 is retained by the clip 32. The clip 32 provides easy and rapid locking and unlocking of the arm 24, to permit positioning and removal of a sample substrate. Any suitable form of clip can be used, and this may comprise a spring-type latch or an element that requires manual actuation.

The head 16 includes a main circular part having a ring 34 of generally uniform cross-section. This ring 34 has a generally planar top surface 36, and a rounded conical bottom surface 38. It defines a central bore 40 which is cylindrical.

A substrate is indicated at 45 and the substrate is chosen to provide good efficiency for particle collection and retention. As such, the substrate 45 is chemically inert, mechanically robust, and does not shed cotton, lint of fluff. It should be formed from a material that is able to withstand high temperatures in any subsequent desorption process, or thermal cleaning process. Preferably, the substrate is a woven sheet material, formed from a single fiber, which has not been subsequently treated by dyes or any other substances, so as to be chemically inert. Substrate 45 could be formed from Teflon (Polytetrafluoroethylene) fibers or cotton, for example.

Where it is desired to use the apparatus 10 close to electrical apparatus and the like, an insulator 42 can be provided between the handle 12 and head 16.

In use, the retaining clip 32 is unlatched, if necessary, to raise the arm end 24 to an open position. A substrate 45 is then located over the bore 40. The apparatus is then closed, by bringing the arm end 24 down until the retaining clip 32 is engaged. This causes the boss 26 and pad 28 to extend into and through the bore 40. Consequently, substrate 45 is shaped to a rounded, domed profile as shown. The substrate 45 then has an exposed working portion 46, outside of and below the bore 40, and an edge or retaining portion 47 trapped between the boss 26 and the head 16. The edge portion 47 extends out through the bore 40 and is sufficiently large to adequately secure and retain the substrate 45. The edge portion 47 should also be large enough to enable the substrate 45 to be readily handled, without contacting the working portion 46. Indeed, to facilitate this, it is possible that the edge portion 47 could be marked or otherwise identified. This could be achieved by colouring the edge portion 47, subject to the requirement that the substrate must be inert.

The substrate 45 could be provided with a coating indicated at 48, to enhance its ability to collect and entrap at least one of desired particles, droplets and chemical agents. The substrate coating can include a chemical treatment to modify the chemistry of the substrate during desorption and pyrolysis cycles. Further, the coating 48 can include means for trapping particles electrostatically.

With the substrate 45 secured in position, the handle 12 can be used to run the working portion 46 of the substrate over surfaces of interest. For example, the working portion 46 can be readily run over the exterior of suitcases, the various surfaces of cars or other vehicles, etc. The apparatus 10 can enable the substrate 45 to access places not readily accessible by hand, for example, areas within the engine compartment of a vehicle, or around suspension and chassis components of a vehicle. It also enables areas around, for example, electrical components or other hazardous locations to be accessed for inspection. It is also possible that the handle 12 can be adapted to be fitted to some extension pole or the like, to further increase the effective range. This would enable various surfaces towards the top of transport trucks or transportation containers, to be readily examined.

Once the required area or surface has been sampled, the retaining clip 32 is released, and the arm end 24 raised to release the substrate 45. The edge portion 47 of the substrate is then grasped, taking care not to contact the working portion 46. Then, as shown in FIG. 5, the substrate 45 is inserted into the desorption stage of an IMS analyzer 50. It will be appreciated that the IMS analyzer 50 is shown purely by way of example, and that the invention is applicable to a wide variety of analyzers, as noted above. IMS analyzers are well known in the art, and are described in U.S. Pat. Nos. such as 5,405,781 and 5,071,771. The substrate 45 is inserted into a platen 51, located above an anvil 52, and this includes means to align the collection or working portion with the analyzer inlet. The anvil 52 is moveable vertically, and is driven by an electromechanical drive 54. The anvil 52 is raised, to press the substrate 45 against an entry port 56 of the IMS analyzer 50. A heater 58, within the anvil 52 is then activated, to vaporize and desorb a sample, indicated at 60 on the substrate 45. The vaporized sample is then entrained in a flow of air or other gas through the anvil 52, indicated at 62 and passes through the entry port 56 into the IMS analyzer 50 for analysis.

The dimensions of the working portion 46 and edge portion 47 and the substrate 45 are such as to correspond with the dimensions of the analyzer 50. Thus, the edge portion 46 abuts a seal 64 around the entry port 56, and the working portion 46 coincides with the heater 58 for desorption.

After desorption, the substrate 45 should effectively be clean. If necessary, all of it can be subject to a subsequent, high temperature cleaning step, to ensure that any remaining contaminants or portions of a previous sample are driven off. The substrate 45 can then be returned to a supply of clean substrates, ready for use.

The shape of the protrusion 26 and pad 28 correspond to the bore 40, to ensure that the substrate 45 is securely retained in position during sampling and to cause the substrate to adopt the desired profile. This prevents the head 16 from becoming contaminated during sampling. Hence, once a substrate 45 bearing a possible sample is removed, the apparatus 10 merely needs to be fitted with a new or clean substrate 45, to be ready for use again. The retaining clip 32 can provide a quick release friction grip.

Figure 2A:
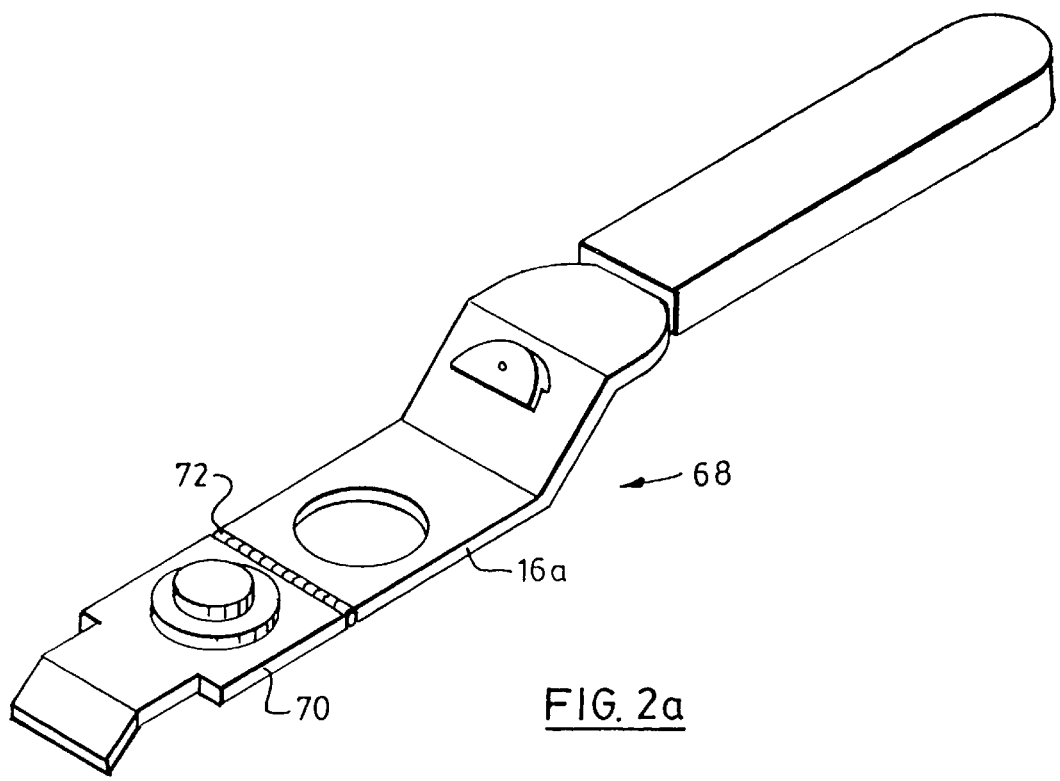
FIG. 2a is a perspective view of a second embodiment of a collection device in accordance with the present invention.
Figure 2B:
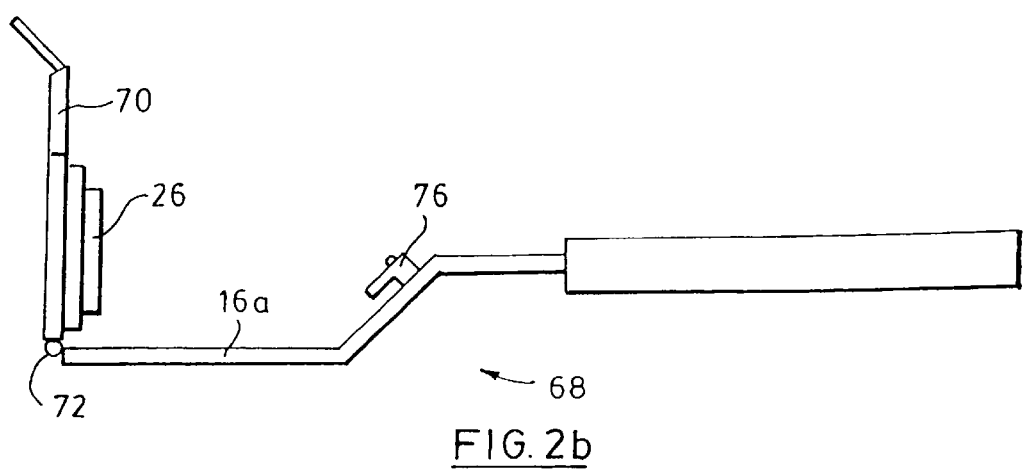
FIG. 2b is a side view of the second embodiment.

FIG. 2 shows an alternative embodiment. For simplicity and brevity, like components are given the same reference as in FIG. 1, and their description is not repeated.

Here, the retaining arm 20 is replaced by a hinged or pivoted plate 70, with the head, here indicated at 16a being provided with a straight edge along which is located a hinge 72. The protrusion or boss 26 and disposable pad 28 are then provided on the plate 70. The plate 70 includes, along its free edge, a clip element 74 that engages a clasp or secondary clip element 76, carried on the portion of the head 16a, joining the head to the handle 12.

Here, the clasp 76 is of a half moon type, which is rotated to engage the clip element 74.

In use, this second embodiment 70 would be used in much the same manner as the first embodiment 10. Again, if desired, an insulator can be provided between the head 16a and handle 12, to permit usage on the electrical equipment and the like.

Figure 3:
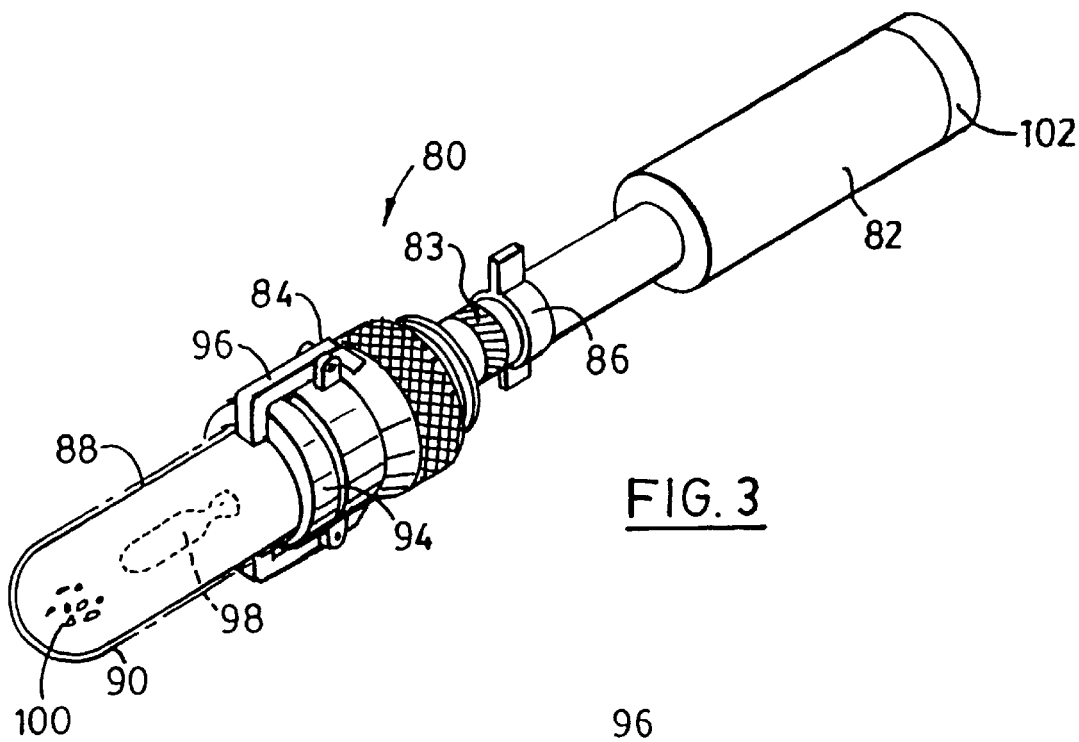
FIG. 3 is a perspective view of a third embodiment of a collection device in accordance to the present invention.
Figure 4A:
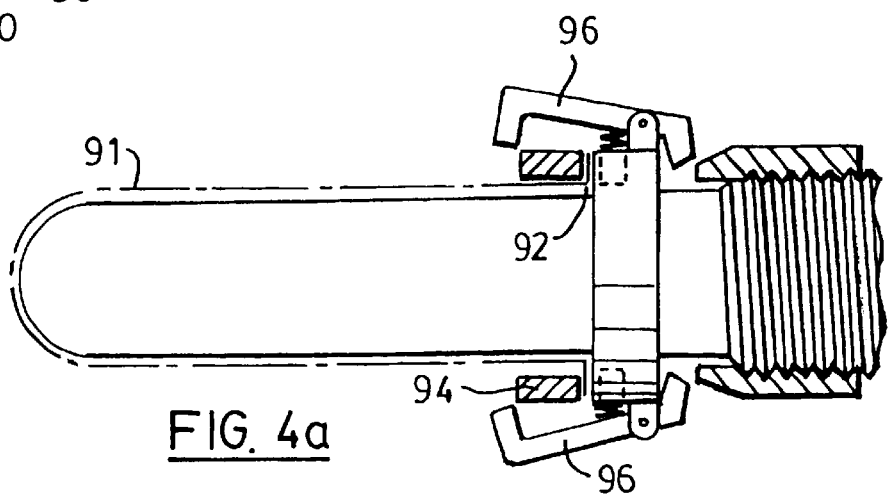
FIGS. 4a and 4b are side views showing engagement of a retaining ring.
Figure 4B:
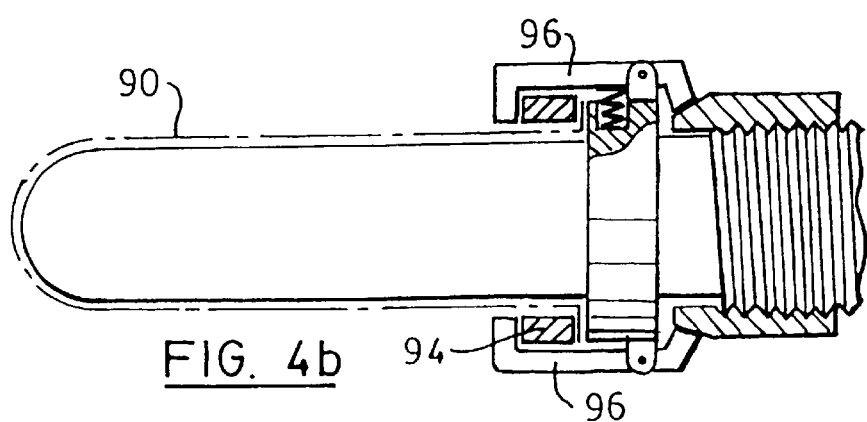

Turning to FIGS. 3 and 4, these show a third embodiment, generally indicated by the reference 80. This third embodiment 80 has a handle 82 connected by an insulator 83 to a head 84.

The head 84 is connected by a quick disconnect fastener 86. This is to enable the head 84 to be removed as an integral part of the substrate, i.e. so that the substrate and head would be treated as a single element. Alternatively, if the substrate is routinely removed from the head, it enables the head 84 to be removed for cleaning and the like.

The head 84 comprises a generally cylindrical body 88 having one free end and another end connected by the insulator 83 to the handle 82. This can be provided with a layer of resilient sponge material or the like, as the layer 28 or the first embodiment, and can have a rounded end.

A substrate is indicated at 90, and is mounted around the head 84. It is preferred to use a generally planar, sheet form substrate 90, which is dimensioned to fit within the inlet of the appropriate analyzer, as for the other embodiments. The substrate 90 will likely need to be folded at the edges, to fully conform to the head 84. The substrate 90, as for the first embodiment, includes a working portion 91 and an edge portion 92.

The edge portion 92 is retained by a retaining ring 94, or any other suitable retaining means adjacent the other end of the head 84. The retaining ring 94 slides over the substrate 90 and traps the edge of the substrate against the base of the body 88. Securing lugs 96 are mounted on the head 84, and the lugs 96 engage and retain the ring 94 in any suitable manner. Here, the lugs 96 are shown as being pivotally mounted with a collar 97 having a conical cam surface, for locking the lugs 96 in an engaged position. The ring 94 could alternatively engage the lugs 96 by a screw or bayonet action, or be provided with magnetic attraction to the head 84, so as to secure the substrate 90 in position.

The head 84 can be formed so as to provide illumination through the substrate 90. For this purpose, the head 84 will need to be, at least to some extent, transparent or translucent. Similarly, the substrate 90 will need to permit transmission of light. Then, a light 98 can be mounted in the head 84. The handle 82 stores batteries, to power the light 98, and an appropriate operating switch can be provided. Additionally, or alternatively, battery power stored in the handle 82 can be used to drive a small suction motor to draw air into and through the head 84, to assist in collecting particles on the substrate 90. Suction holes, indicated at 100 could then be provided on the head 84. The handle 82 can include a handle cap 102, for replacement of batteries, in known manner.

In use, this embodiment is used in a similar manner to the other embodiments. A substrate 90 is mounted on the head 84 and run over surfaces of interest. Again, an extension of handle (not shown) can be provided. After collection of a sample, either the substrate 90 is removed from the head 84, or the whole head 84 is removed, by way of the quick disconnect fastener 86. Where it is possible that the head 84 may have become contaminated, then it will be desirable to replace the head 84 with another head that has been cleaned. In any event, to insert the substrate 90 into an analyzer, it will be removed from the head 84 together with the ring 94, again by just grasping the edge portion 92, to prevent contamination of an operator's hands. The ring 94 will then be carefully removed and the substrate 90 is then inserted into the analyzer inlet.

While preferred embodiments have been described, it will be appreciated that numerous variations and modifications are possible within the scope of the present invention. Various arrangements can be conceived to follow the sampling concept of non-contact between the substrate and the searcher's hands so as to avoid contamination, an aspect of the greatest concern to organizations such as police, army and customs services engaged in search operations. Recognizing that current, sensitive analytical instruments can detect as low as 1 pg levels of drugs and explosives, it will be appreciated just how critical it becomes to keep the searcher's hands free from close contact with the substrate. The searcher will be instructed to carefully remove the substrates for presentation to the analyzer, by carefully handling the substrate at its edge. It is also to be appreciated that the substrate can be composed of electrically conducting mesh, of a size appropriate to the particle range to the collected. Then the conductive mesh substrate can be used directly in a desorbing/pyrolysis stage in which the particles are flash desorbed by the rapid heating of the metal mesh by the passage of electric current through it. The substrate can also be such as to attract and hold particles, droplets etc., electrostatically. The substrate can also be chemically treated to enhance its ability to collect and entrap substances that the user wishes to collect, such as particles, droplets and chemical agents. Thus, the substrate can be chemically treated to modify the chemistry thereof during desorbtion and pyrolysis cycles, to enhance collection of the desired substances.

The present invention has the advantage that the profile of the substrate is sufficiently raised, during sampling, to allow good all-around contact with the surfaces/objects under inspection. The substrate is pressed through the bore of the head aperture in the sampler to contact the surfaces or objects to be sampled. The handle allows extended reach to access more difficult areas, or areas which might be hot, dirty or be close to moving machinery or electrical sources. Telescopic extensions can be provided to the handle to obtain samples from locations normally out of the reach of the person using a swab/glove or hand covering. There is ease in decontamination because the scrubber pad is easily removed and discarded. Since the pads are small and are of low cost to manufacture, there is no economic disadvantage in using this discard protocol.

The collection substrate is presented to the analyzer by inserting the substrate into a slot of matching geometrical shape and size which is then transposed to the desorption stage, so no intermediate sample transfer step is required. At the desorption stage, and anvil is raised, heated and sealed against the inlet to an IMS analyzer. A key benefit of controlling the geometry of the substrate surface which can be allowed to make contact with the surfaces under inspection is that it can be made to match the analyzer inlet geometry perfectly. That is, the analyte is centrally collected and correspondingly aligned and presented to the analyzer. The IMS analyzer has sufficient sensitivity for the detection of the desired analytes, and their identifications are pre-programmed into the IMS analyzer. Analyzers such as the IMS have been well described in the literature and have also been the subject of numerous patents. While the invention is described in terms of analysis using IMS, it will be obvious to those experienced in the art that the substrates can be made into forms and shapes suitable for introduction to other types of analyzers, such as gas chromatographs or chemi-luminescent detectors, mass spectrometer and the like.

We claim:

1. A method of collecting a sample of at least one of particles, aerosols, droplets and trace chemicals, the method comprising the steps of:

(1) providing a substrate having a central working portion and an edge portion substantially extending around the working portion and mounting the substrate in a hand held sampling apparatus comprising a handle, a head connected to the handle and means retaining the substrate, by the edge portion of the substrate, on the head, so that the working portion of the substrate is presented for use;

(2) manipulating the apparatus so that the collection portion of the substrate traverses surfaces of interest;

(3) removing the substrate from the apparatus by grasping an edge portion thereof without contacting the working portion, and inserting the substrate into the inlet port of an analyzer;

(4) operating the analyzer to desorb any sample collected and analyzing the sample.

2. A method as claimed in claim 1, when carried out with an analyzer which has a heatable anvil which can be raised against the inlet port, and which has provision for a gas flow, wherein steps (3) and (4) comprise:

(a) placing the substrate between the anvil and the inlet port;

(b) displacing the anvil towards the inlet port, to seal the substrate between the anvil and the inlet port;

(c) heating the anvil to heat the substrate to desorb and vaporise any sample present;

(d) providing a flow of gas through the anvil and the substrate into the inlet port, to entrain any vaporised sample;

(e) operating the analyzer to detect substances of interest.

3. A method as claimed in claim 1, or 2 which includes mounting the substrate by substantially all of the edge portion thereof and causing the central working portion to project outwardly from the edge portion, for contact with surfaces of interest.

4. A method as claimed in 3, which includes: providing the head with a retaining means, a bore and a projection means; and the method comprising spacing the projection and retaining means apart in an open configuration to permit insertion of the substrate, and pressing the projection means and the retaining means together into a closed configuration, to trap the edge portion of the substrate between the projection and retaining means with projection means causing the working portion to project outwardly, the projection means and the retaining means being subsequently displaced to the open configuration for removal of the substrate.

5. A method as claimed in claim 4, which includes providing the projection means with a boss and a resilient layer, providing resilient support to the substrate.

6. A method as claimed in claim 4, which includes providing an arm pivotally mounted to the handle and mounting the projection means on one end of the arm, and providing a retaining clip means between the handle and the other end of the arm for retaining the arm in a closed configuration, in which the retaining and projection means engage and secure the substrate, the method including: pivoting the arm and the handle to the open configuration; inserting the substrate; pivoting the handle and the arm to the closed configuration to trap the edge portion of the substrate between the projection and retaining means, and securing the arm and the handle in the closed configuration with the retaining clip means; and, after traversing the substrate over surfaces of interest, releasing the retaining clip means, displacing the arm and the handle to the open configuration and removing the substrate for insertion into the inlet part of the analyser.

7. A method as claimed in claim 3, which comprises providing the head with a projecting body and mounting the substrate around the projecting body, and providing the retaining means at the end of the projecting body remote from a free end thereof.

8. A method as claimed in claim 7, which includes providing the retaining means in the form of a ring, and wherein after mounting of the substrate on the projecting body, the method includes sliding the ring over the substrate to retain the substrate in position, and after collection of a sample by traversing the substrate over surfaces of interest, displacing the ring off the substrate to permit removal of the substrate.

9. A method as claimed in claim 7, which includes providing illumination from within the projecting body to illuminate a surface being sampled.

10. A method as claimed in claim 7, which includes providing a plurality of holes in the projecting body and drawing air through the substrate and through those holes, to enhance collection of particles on the substrate.

11. A method as claimed in claim 1, or 2 which includes providing a substrate which is chemically inert, is devoid of any dyes or coloring materials and is such as to be capable of a mechanical wiping action without removing from the substrate appreciable amounts of lints and fibers.

12. A method as claimed in claim 11, which includes treating the substrate by one of: a chemical treatment to enhance its ability to collect and entrap at least one of desired particles, droplets and chemical agents; and a treatment to modify the chemistry of the substrate during desorption and pyrolysis cycles.

13. A method as claimed in claim 11, which includes providing a substrate which is woven and comprises one of cotton, polytetrafluoroethylene and fiberglass.

* * * * *